(12) United States Patent
Schwarz et al.

(10) Patent No.: US 7,557,188 B2
(45) Date of Patent: Jul. 7, 2009

(54) METHODS OF TREATING BLOOD COAGULATION DISORDERS USING A PHARMACEUTICAL PREPARATION COMPRISING VWF PROPEPTIDE

(75) Inventors: Hans-Peter Schwarz, Vienna (AT); Katalin Varadi, Vienna (AT); Peter Turecek, Klosterneuburg (AT); Hendrik Coenraad Hemker, Maastricht (NL); Suzette Lucette Beguin, Maastricht (NL)

(73) Assignee: Baxter Innovations GmbH, Vienna (AT)

( * ) Notice: Subject to any disclaimer, the term of this patent is extended or adjusted under 35 U.S.C. 154(b) by 145 days.

(21) Appl. No.: 11/218,406

(22) Filed: Sep. 2, 2005

(65) Prior Publication Data
US 2006/0003921 A1 Jan. 5, 2006

Related U.S. Application Data (63) Continuation of application No. 09/424,498, filed as application No. PCT/EP98/03090 on May 26, 1998, now Pat. No. 7,005,502.

(30) Foreign Application Priority Data

May 28, 1997 (AT) ...................................... 917/97

(51) Int. Cl.
*A61K 35/14* (2006.01)
*A61K 38/00* (2006.01)
(52) U.S. Cl. .................. 530/380; 530/383; 530/395; 514/2; 514/802; 514/822; 435/69.6; 435/13
(58) Field of Classification Search ............... None
See application file for complete search history.

(56) References Cited

U.S. PATENT DOCUMENTS

| | | | | |
|---|---|---|---|---|
| 4,160,025 | A | 7/1979 | Eibl et al. ............ 424/101 |
| 4,395,396 | A | 7/1983 | Eibl et al. ............ 424/101 |
| 4,640,834 | A | 2/1987 | Eibl et al. ............ 424/94 |
| 4,814,277 | A | 3/1989 | Eibl et al. | |
| 5,571,784 | A | 11/1996 | Reers et al. | |
| 5,610,147 | A | 3/1997 | Seelich | |
| 5,614,405 | A | 3/1997 | Eibl et al. ............ 435/236 |
| 5,639,730 | A | 6/1997 | Eibl et al. | |
| 5,714,370 | A | 2/1998 | Eibl et al. ............ 435/214 |
| 5,733,885 | A | 3/1998 | Eibl et al. ............ 514/21 |
| 5,849,702 | A * | 12/1998 | Garfinkel et al. ....... 514/12 |

FOREIGN PATENT DOCUMENTS

| | | |
|---|---|---|
| AT | 350 726 | 6/1979 |
| AT | 368 883 | 11/1982 |
| AT | 398 079 B | 9/1994 |
| AT | 404 359 B | 11/1998 |
| AT | 404 554 B | 12/1998 |
| CA | 1239583 | 7/1988 |
| CA | 2071567 | 12/1992 |
| EP | 0 131 740 A2 | 1/1985 |
| EP | 0 159 311 A1 | 10/1985 |
| EP | 0 247 998 A2 | 12/1987 |
| EP | 0 519 901 A2 | 12/1992 |
| EP | 0 131 740 B2 | 9/1994 |
| EP | 0 637 451 A1 | 2/1995 |
| JP | 07330797 | 12/1995 |
| WO | WO 94/13329 | 6/1994 |
| WO | WO 97/41206 | 6/1997 |

OTHER PUBLICATIONS

Seffernick et al., J. Bacteriology, vol. 183, pp. 2405-2410, 2001.*
Borchiellini, Alessandra, et al; Quantitative Analysis of von Willebrand Factor Propeptide Release In Vivo: Effect of Experimental Endotoxemia and Administration of I-Deamino-8-D-Arginine Vasopressin in Humans; *Blood;* Oct. 15, 1996; pp. 2951-2958, vol. 88, No. 8.
Lenting, Peter J., et al.; The Life Cycle of Coagulation Factor VIII in View of its Structure and Function; *Blood;* Dec. 1, 1998; pp. 3983-3996; vol. 92, No. 11.
Stedman's Medical Dictionary; 26th Edition; copyright 1995; p. 1300.
Turecek, Peter I., et al., In vivo and in vitro processing of recombinant pro-von Willebrand factor; *Histochem Cell Biol;* 2002; 123-129; vol. 117.
Váradi, Katalin, et al.; Thrombin-mediated In Vitro Processing of Pro-von Willebrand Factor; *Thromb Haemost.* 2001: pp. 1449-1458; vol. 86.
Wagner, Denisa D, et al.; Divergent fates of von Willebrand factor and its propolypeptide (von Willebrand antigen II) after secretion from endothelial cells; *Proc. Natl. Acad. Sci USA;* Apr. 1987; pp. 1955-1959; vol. 84.
Official Action for A917/97 dated Dec. 12, 1997 (translation).

(Continued)

*Primary Examiner*—Andrew D Kosar
*Assistant Examiner*—Kagnew H Gebreyesus
(74) *Attorney, Agent, or Firm*—Townsend and Townsend and Crew, LLP (57) ABSTRACT

Described is a pharmaceutical preparation for treating blood coagulation disorders comprising an effective amount of vWF propeptide as well as a method for producing such a preparation.

7 Claims, 4 Drawing Sheets

OTHER PUBLICATIONS

Blann, A.D. et al., "von Willebrand Factor, Endothelial Cell Damage and Atherosclerosis", *Eur. J. Vasc. Surg.*, vol. 8, 1994, pp. 10-15.

Borchiellini, A. et al., "Quantitative Analysis of von Willebrand Factor Propeptide Release in vivo: Effect of Experimentation Endotoxemia and Administration of 1-Deamino-8-D-Arginine Vasopressin in Humans", *Blood*, vol. 88, 1996, pp. 2951-2958.

Eikenboom, J.D.J. et al., "The Inheritance and Molecular Genetics of von Willenbrand's Disease", *Haemophilia,* , vol. 1, 1995, 77-90.

Fisher B.E. et al., "Structural Analysis of Recombinant von Willebrand Factor; Identification of Hetero- and Homo-dimers", *FEBS Letters*, vol. 351, 1994, pp. 345-348, Abstract # XP-002078562.

Fisher B.E. et al., "Structural Analysis of Recombinant von Willebrand Factor Produced at Industrial Scale Fementation of Transformed CHO cells co-expressing Recombinant Furin", *FEBS Letters*, vol. 375, 1995, pp. 259-262, Abstract # XP-002078561.

Isobe, T. et al., "Propolypeptide of von Willebrand Factor Is a Novel Ligand for Very Late Antigen-4 Integrin", *J. of Biol. Chem.*, vol. 272, 1997, pp. 8447-8453, Abstract # XP-002078564.

Lankhof H. et al., "von Willebrand Factor Without the A2 Domain Is Resistant to Proteolysis", *Thromb. and Haemostasis*, vol. 77, 1997, pp. 1008-1013.

Leyte A. et al., "The Pro-polypeptide of von Willebrand Factor is Required for the Formation of a Functional Factor VIII-Binding Site on Mature von Willebrand Factor", *Biochem.*, vol. 274, 1991, pp. 257-261, Abstract # XP-002078565.

Takagi, J. et al., "A Collagen-binding Glycoprotein From Bovine Platelets Is Identical to Propolypeptide of von Willebrand Factor", *J. of Biol. Chem.*, vol. 264, 1989, pp. 10425-10430.

Takagi J. et al., "Inhibition of Platelet-Collagen Interaction by Propolypeptide of von Willebrand Factor", *J. Biol. Chem.*, vo. 264, 1989, pp. 6017-6020, Abstract # XP-002078563.

* cited by examiner

Fig 1: The effect of provWF on the thrombin generation in plasma in the presence of platelets.

Fig 2: Dose dependent effect of provWF on the thrombin generation in plasma in the presence of platelets.

Fig. 3a Comparison of the in vivo effect a recombinant vWF (pro-vWF) and plasma derived vWF preparation in a dog

Fig. 3b

METHODS OF TREATING BLOOD COAGULATION DISORDERS USING A PHARMACEUTICAL PREPARATION COMPRISING VWF PROPEPTIDE

This application is a continuation of U.S. patent application Ser. No. 09/424,498, filed Nov. 24, 1999, which is a U.S. National Phase Application of PCT/EP98/03090, filed May 26, 1998, which claims the benefit of Austrian Patent Application No. A 917/97, filed May 28, 1997, the disclosures of which are hereby incorporated by reference in their entirety for all purposes.

FIELD OF THE INVENTION

The invention relates to a pharmaceutical preparation comprising the vWF-propeptide (pp-vWF).

BACKGROUND OF THE INVENTION

Von Willebrand factor (vWF) is a glycoprotein circulating in plasma as a series of multimers ranging in size from about 500 to 20,000 kD. Multimeric forms of vWF are composed of 250 kD polypeptide subunits linked together by disulfide bonds. vWF mediates the initial platelet adhesion to the subendothelium of the damaged vessel wall, only the larger multimers also exhibiting hemostatic activity. It is assumed that endothelial cells secret large polymeric forms of vWF and that those forms of vWF which have a low molecular weight (low molecular weight vWF) have arisen from proteolytic cleavage. The multimers having large molecular masses are stored in the Weibel-Pallade bodies of the endothelial cells and liberated upon stimulation.

vWF is synthesized by endothelial cells and megakaryocytes as prepro-vWF that consists to a large extent of repeated domains. Upon cleavage of the signal peptide pro-vWF dimerizes through disulfide linkages at its C-terminal region. The dimers serve as protomers for multimerization which is governed by disulfide linkages between the free end termini. The assembly to multimers is followed by the protelytic removal of the propeptide (Leyte et al., Biochem. J. 274 (1991), 257-261).

The full length of cDNA of vWF was cloned; the propolypeptide corresponds to amino acid residues 23 to 764 of the full length prepro-vWF (Eikenboom et al (1995) Haemophilia 1, 77-90).

The propeptide of vWF (pp-vWF) was shown to be identical to the von Willebrand antigen II, the second identified antigen that is deficient in the plasma and platelets of patients with severe von Willebrand disease (vWD). pp-vWF is specifically localized in platelets since plasma contains less than 5% of total propeptide vWF in blood, assuming the platelet count is $3\times10^8$ per ml. As already known, pp-vWF is released from platelets upon activation by various agonists. The pp-vWF is a glycoprotein not only because it reacts with periodic acid Schiff's reagent but also because it binds to lentil lectin. pp-vWF binds specifically to native type I collagen, but does not bind to heat-denatured collagen. It was shown that the affinity between pp-vWF and type I collagen was quite high so that the binding—which does not require any divalent cation and is not affected by addition of a peptide that contains sequence of arginine-glycine-aspartic acid (that is known to inhibit many cell attachment processes)—rapidly reached equilibrium.

The physiological role of pp-vWF is postulated to lie in the government of the assembly of vWF multimers, either before or after the cleavage from pro-vWF molecules. (Takagi et al., JBC 264 (18) (1989), 10425-10430).

pp-vWF was also shown to inhibit the platelet collagen interaction action (Takagi et al., JBC 264 (11) (1989), 6017-6020).

In Isobe et al. (JBC 272 (13) (1997), 6447-6453) the role of pp-vWF as a novel physiological ligand and an adhesion substrate for $\alpha 4\beta 1$ integrin-expressing leukemia cells was investigated. It was found that pp-vWF plays an important role in the mechanism underlying the melanoma metastasis as well as vascular inflammation.

Although pharmaceutical preparations containing mature vWF are known (see e.g. U.S. Pat. No. 5,571,784) the pharmaceutical usage of pp-vWF or the pro-form vWF have not been described or suggested in the prior art. According to the U.S. Pat. No. 5,571,784 vWF does not impair the systemic anticoagulatory effect of the anticoagulant hirudin as measured by the aPTT, rather it decreases the bleeding side effects of anticoagulant therapy. vWF is therefore proposed as a pseudo-antidote in assocation with hemorrhages which are produced by administering antithrombotic and/or fibrinolytic agents.

From Blann et al. (Eur. J. Vasc. Surg. 8 (1994), 10-15) it is also known that vWF levels are increased with risk factors for atherosclerosis and in patients with diffuse arterial disesase. The level of vWF is also thought to be a measure of endothelial$_4$>integrin-expressing leukemia cells was investigated. It was found that pp-vWF plays an important role in the mechanism underlying the melanoma metastasis as well as vascular inflammation.

From Blann et al. (Eur. J. Vasc. Surg. 8 (1994), 10-15) it is also known that vWF levels are increased with risk factors for atherosclerosis and in patients with diffuse arterial disesase. The level of vWF is also thought to be a measure of endothelial damage in the inflammatory vasculitides. Providing low levels of vWF in a patient is suggested to be protective for such diseases.

SUMMARY OF THE INVENTION

It is the object of the present invention to provide a vWF pharmaceutic with improved properties. The preparation should enhance the intrinsic blood coagulation activity in individuals and reduce the arterial thrombotic risk of vWF therapy.

This object is solved by the present invention by providing a pharmaceutical preparation for treating blood coagulation disorders comprising an effective amount of vWF propeptide. It was found out that pp-vWF plays an essential role in blood coagulation. It promotes the intrinsic blood coagulation and thereby acts on secondary hemostasis. At the same time it inhibits the platelet adhesion and controls the primary hemostatic activity of mature vWF by binding to collagen. Based on these findings, a vWF preparation can be improved providing additional pro-vWF or pp-vWF as a separate effective protein in the vWF preparation. pp-vWF controls the primary hemostatic activity of the mature vWF and thus reduces the potential thrombotic risk of vWF, for example inducing arterial thrombosis as indicated by the prior art.

It was surprisingly found out that a recombinant vWF preparation (rvWF) containing substantial amounts of pp-vWF induces an elevated thrombin generation in vitro. The thrombin generation was measured by an in vitro assay performed with washed vWD platelets in FVIIIC substituted vWD plasma upon addition of FEIBA (factor VIII inhibitor bypassing activity; Austrian patents No 350 726, 368 883 and 398 079) to initiate the activation of prothrombin. When the rvWF preparation contained a predominant amount of pro-vWF and pp-vWF the thrombin generation was substantially increased. The contribution of the pp-vWF to the coagulation-promoting effect of vWF is therefore surprisingly significant.

Since these results imply that the effect of vWF as blood coagulation factor is related to pp-vWF, the pharmaceutical preparation based on the pp-vWF or pro-vWF is applicable in areas wherein vWF has been proposed and even more areas where a coagulation-promoting effect is desired.

DETEAILED DESCRIPTION

The preparation of the pp-vWF or pro-vWF is well known in the art due to many papers relating to expression and properties of vWF or for diagnostic purposes, see e.g. experimental procedures in Isobe et al., Takagi et al. (both 1989 papers) or Leyte et al. However, there was not yet any individual coagulation promoting activity reported to be associated with vWF and the propeptide region of vWF and therefore not a respective pharmaceutical preparation. Since the pp-vWF is a well defined polypeptide and easily prepared by recombinant DNA-technology, the recombinant way of production is a preferred embodiment for producing the present pharmaceutical preparation. The polypeptide may also be purified or purified further by chromatography, such as by ion exchange chromatography and/or affinity chromatography using monoclonal antibodies, heparin, collagen, factor VIII protein, or fragments thereof as affinity ligands. It is also possible to separate pp-vWF from contaminating proteins and/or mature vWF by gel filtration.

A preferred embodiment of the present invention is a pharmaceutical preparation essentially consisting of the vWF-propeptide. Thereby the preparation contains purified pp-vWF or pro-vWF to the extent that at least 80%, preferably at least 90%, most preferred more than 95% or about 100% pure pp-vWF or pro-vWF is contained.

Another embodiment of the present invention is a preparation essentially consisting of the pro-vWF containing the vWF-propeptide as a pharmaceutical preparation.

As stated above it is preferred to use recombinantly produced pro-vWF or pp-vWF for the present preparation. (FEBS Letters 351 (1994), 345-348 or Blood 88 (8) 19996, 2951-2958)

The preparations of the present invention preferably contain at least 10 nM pp-vWF, more preferably at least 30 nM, especially more than 50 nM, and/or at least 10 nM pro-vWF, more preferably more than 100 nM, especially more than 250 nM. The effective amount is defined to obtain a pp-vWF level of at least twice the physiologic amount in human plasma. In Blood 88 (8) 1996, 2951-2958 it is reported that the molar ratio of the propeptide and vWF concentration is about 0,1 in Normal Plasma. The pp-vWF is considered as a rather abundant protein at a concentration of 5 to 100 nmol/L depending on the state of activation of the endothelium.

If vWF is contained in the preparation besides pro-vWF the molar ratio of the pro-vWF and vWF is at least 10%, which may be measured as U-Antigen detected by a polyclonal antibody preparation directed against vWF antigen. In the preferred preparation according to the invention the molar ratio is even higher, at least 20% or more preferred at least 50%. The most effective preparation according to the invention contains more than 80% of vWF-Antigen as pro-vWF.

It turned out that a pharmaceutical preparation according to the invention based on pro-vWF is rapidly processed upon administration in vivo. The thus generated pp-vWF is effective in its thrombin potential and coagulation-promoting activity.

In another preferred embodiment the pharmaceutical preparation according to the present invention further contains a hemostasis protein, preferably a blood factor. Preferred embodiments of these blood factors are selected from the group consisting of mature vWF, factor VIII, activated blood coagulation factors, blood factors with FEIB-activity and FEIBA. Any hemostasis protein decreasing the aPTT or PT of normal plasma is a suitable combination with the pp-vWF or pro-vWF.

A combination of the pp-vWF preparation with FVIIIC provides for a pharmaceutical preparation with improved coagulation activity. When the propeptide is in the form of pro-vWF that is complexed to FVIIIC, the pharmaceutical preparation according to the present invention shows additionally improved FVIIIC-stability.

The further combinations in a pharmaceutical preparation according to the invention are provided with a platelet component. Some of the components having binding properties or activity to vWF or pro-vWF or pp-vWF, which are suitable to contribute to the physiological activities, are collagen, platelet glycoprotein, a platelet, fibrinogen, fibrin, heparin, or a derivative thereof.

The pharmaceutical preparation of the present invention may also further contain phospholipids.

The pharmaceutical preparation according to the present invention preferably has been made virus safe by treating for virus inactivation or removal.

The virus inactivation or removal treatment may be performed by any treatment accepted as being efficient. According to preferred embodiments of the present invention the pharmaceutical composition is treated with tensides and/or heat, e.g. by a heat treatment in the solid state, especially a steam treatment according to EP 0 159 311 or EP 0 519 901 or EP 0 637 451, by a hydrolase treatment according to EP 0 247 998, by a radiation treatment or by a treatment with chemical or chemical/physical methods, e.g. with chaotropic agents, according to WO 94/13329, by a treatment with organic solvents and/or tensides according to EP 0 131 740 or photoinactivation. Nanofiltration also represents a preferred method of depleting viruses within the scope of the present invention.

The pharmaceutical preparation according to the present invention further contains a pharmaceutically acceptable carrier and/or suitable buffer auxiliary preserving and/or stabilizing substances like carbohydrates or salts, or protease inhibitors or cofactors, respectively. The preparation is finally formulated for especially parenteral or topical uses like any known vWF preparation according to the prior art. This may be done by filling it into containers in a form suitable for administration and preferably packing it so as to be storage stable, optionally in the lyophilized or frozen state.

The preparation according to the present invention may be produced both by purification from blood serum or plasma and by a respective expression system. Transgenic animals might as well provide the source of pp-vWF or pro-vWF.

A preparation according to the present invention may also be provided by expression of the pp-vWF or the pro-vWF containing pp-vWF in vivo or ex vivo. Especially suitable for such procedure are cells derived from mammals, in particular human cells, which can be cultured or employed in human gene therapy. Also transformed cells expressing pp-vWF or the pro-vWF as a heterologous protein are a suitable source for obtaining the preparation according to the invention.

A further embodiment according to the present invention is also a pharmaceutical preparation containing a pro-vWF mutant with a mutation at the cleavage site. Such a mutant has been described by Borchiellini et al. for experimental purposes (Blood 88 (8), 2951-2958 (1996)). The described vWF-Gly 763 has a mutation which provides for a pro-vWF that is unclearable by physiological enzymes. The resistance of the pro-vWF against cleavage leads to the prolonged half-life of the coagulation-promoting activity of the pp-vWF being comprised in the pro-vWF form. Thereby a prolonged action is designed by a specific mutation at the cleavage site.

This specific mutation might by effected by the techniques of Lankhof et al. (Thrombin and Haemostasis 77 (5), 1008-13 (1997)) who produced a deletion mutant lacking the A2 domain, which was resistant to proteolysis unless it became sensitive upon unfolding to the molecule.

Other mutant proteins of pp-vWF or pro-vWF that exhibit the properties of the native proteins may also be used for the present preparations. In this case it is preferred to employ an analogue or mutant having at least 80% homology and the function to act as a modified pp-vWF or pro-vWF.

Yet another effect of the present invention is a method for producing a pharmaceutical preparation containing an effective amount of pp-vWF comprising providing a source material containing the vWF propeptide, separating the pp-vWF from the source material and formulating the pp-vWF to a pharmaceutical preparation.

Source material may preferably be blood, serum, blood fractions, colostrum or milk of transgenic animals, or cell culture solutions, especially from cells that have been produced by recombinant DNA-technology. The source material containg pp-vWF preferably contains the pp-vWF in a pro-vWF. Methods and techniques are described in FEBS Letters 351, 345-348 (1994) or Borchiellini et al. supra.

The expression is preferably performed in a way to prevent the processing and maturation of vWF to obtain the pro-vWF. This may be effected by the omission or inhibition of processing enzymes. The inhibition of processing enzymes like furin or PACE or the multimerase as described in A 770/96 and 769/96 prevents the premature processing of pro-vWF to vWF. On the other hand the pp-vWF might be expressed as a separate protein or obtained upon cleavage and processing of the pro-vWF in vitro.

Yet another preferred embodiment of the present invention is conducting the method by providing a source material containing the pro-vWF as a mutant pro-vWF with a mutation at the cleavage site of the pp-vWF, such as an amino acid change at 763 like pro-vWF-Gly 763.

Alternatively, the pharmaceutical preparation may be produced in the presence of an inhibitor inhibiting the cleavage of the pp-vWF from the pro-vWF. Examples for such inhibitors are antibodies against the cleavage site or a binding peptide directed against the cleavage site or inhibitor of processing enzyme.

As stated above, the preparation and separation steps of pp-vWF are well-known in the art due to various reports of the experiments conducted with pp-vWF (see Isobe et al., Tagaki et al., Leyte et al.).

Of course, the method according to the present invention preferably exhibits a treatment for inactivating or removing viruses, since the pp-vWF is a biological protein and in a form which is administered to humans.

The invention further provides pp-vWF and/or pro-vWF for use as a medicine. The effective dose to elevate the pp-vWF level in vivo to at least twice the physiological amount may be provided by administering the pp-vWF or the pro-vWF once or several times a day. Due to the rather short half-life of the pp-vWF in vivo it might be necessary to administer the protein frequently during the acute disorder.

Yet another aspect of the present invention is the use of pp-vWF and/or pro-vWF containing the pp-vWF for the preparation of a pharmaceutical composition for treating a patient at a risk of blood coagulation disorders, such as vWD, hemophilia (e.g. phenotypic hemophilia, hemophilia A and factor VIII inhibitors).

The effective dosage of the preparation when applied will vary depending on the respective syndrome and preferably should be chosen after determination of the blood levels of the critical blood factors or risk for thrombosis in the patient. The optimum dosage also depends on whether or not the parenteral, preferably intravenous, subcutaneous or intramuscular administration is to be effected in bolus form or as a depot. By using a suitable carrier material such as liposomes a peroral administration is feasible. It also depends on whether it is to be applied systemically and/or locally at the site of the blood coagulation disorder.

Therefore, the invention also provides for a method of treating a patient at a risk of blood coagulation disorders comprising administering to said patient an effective amount of vWF-propeptide or pro-vWF. Preferably, a patient suffering from vWD, phenotypic hemophilia, hemophilia A or factor VIII inhibitors is treated according to the invention.

Due to the positive properties pp-vWF or pro-vWF exhibit when combined with preparations with a risk for arterial thrombosis, such as vWF-preparations, it is another aspect of the present invention to use pp-vWF or pro-vWF to reduce thrombosis risk in vWF-preparations. Thereby the potential exaggeration of arterial thrombus formation is effectively down-modulated, whereas the intrinsic and extrinsic blood coagulation is promoted in case of a coagulation deficiency.

In particular the compatibility of a vWF preparation is ameliorated and improved by the addition of and combination with the pp-vWF or pro-vWF in effective amounts. Because of the controlling function of the vWF propeptide it further contributes to the treatment and prevention of adverse reactions of endogenous and exogenous vWF, particularly elevated vWF levels in patients associated with thrombotic thrombocytopenic purpura, Henoch Schönlein purpura, pre-clampsia, neonatal thrombocytopenia or hemolytic uremic syndrome, myocardial infarction or a poor outcome following arterial surgery.

EXAMPLES

1. The Effect of provWF an ppvWF on the Thrombin Generation in Plasma in the Presence of Platelets Severe vWD plasma (George King Bio-Medical Inc., USA) which was previously reconstituted with 1 U/ml FVIIIC (Recombinate, Baxter, USA) (200 μl) was incubated with 50 μl washed platelets from a severe vWD patient (Type III) in the presence of 0.1 U/ml FEIBA (Immuno, Austria) and 16 mM $CaCl_2$. Alternatively FVIIa could also be used as an activator, preferably in a final concentration of 0.2 μg/ml. Subsamples of 10 μl were withdrawn at time intervals, and added to 300 μl chromogenic substrate for thrombin (D-cyclohexyl-gly-L-Ala-L-Arg-pNA; Immuno, Austria) containing 3 mM EDTA to stop any further reactions. The reaction was stopped by the addition of 100 μl of 75% (v/v) acetic acid, and the absorbance, which is the function of the thrombin concentration, was measured at 405 nm.

Two different vWF preparations (containing lower and higher amounts of provWF and propeptide) were added to the factor VIII reconstituted plasma samples in a final concentration of 1 Risto U/ml, and thrombin generation was followed. (1 Risto U/ml=the ristocetin cofactor activity of the vWF in normal plasma). Thus the plasma samples contained in the case of the preparation with the low provWF and low propeptide 0.24 nM provWF and 0.19 nM propeptide, while the other one contained 34 nM provWF and 4 nM propeptide, respectively.

Figure 1:
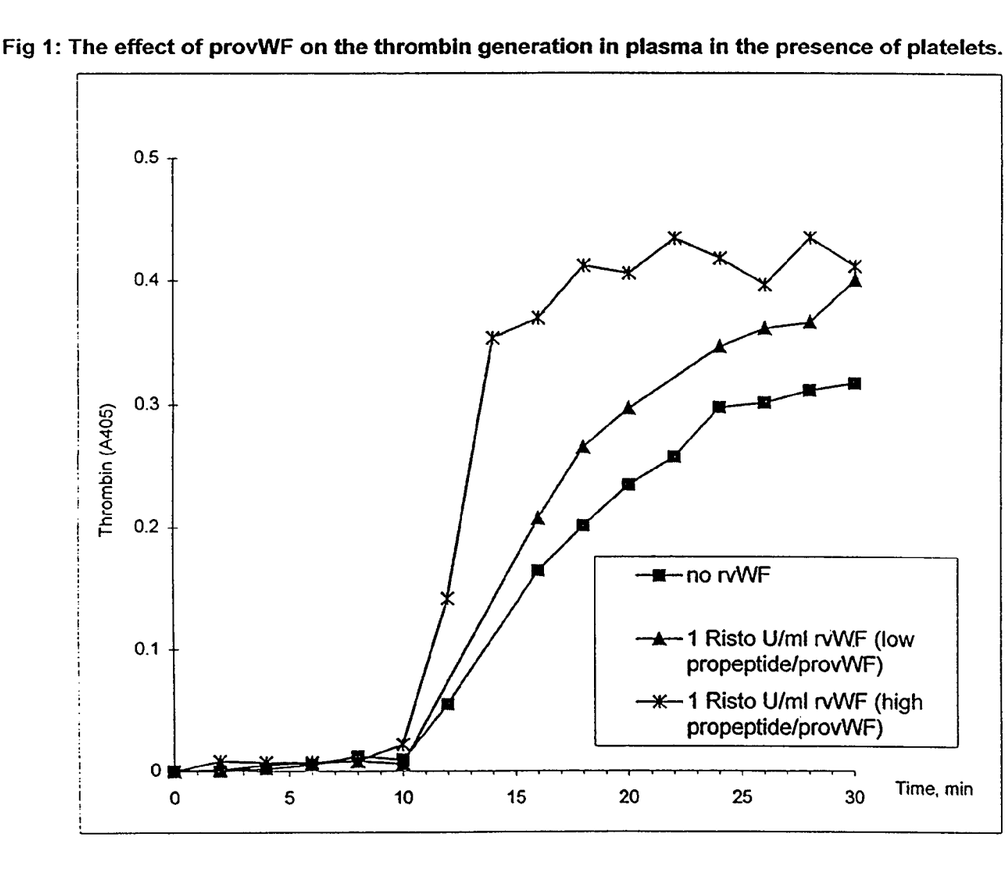
FIG. 1 shows the effect of pro-vWF on the thrombin generation in plasma in the presence of platelets.

The results are depicted on FIG. 1.

It is clear from the curves, that albeit both preparations increased the rate of thrombin generation, the high provWF and high propeptide containing product had a stronger effect and produced the enhanced thrombin generation.

Figure 2:
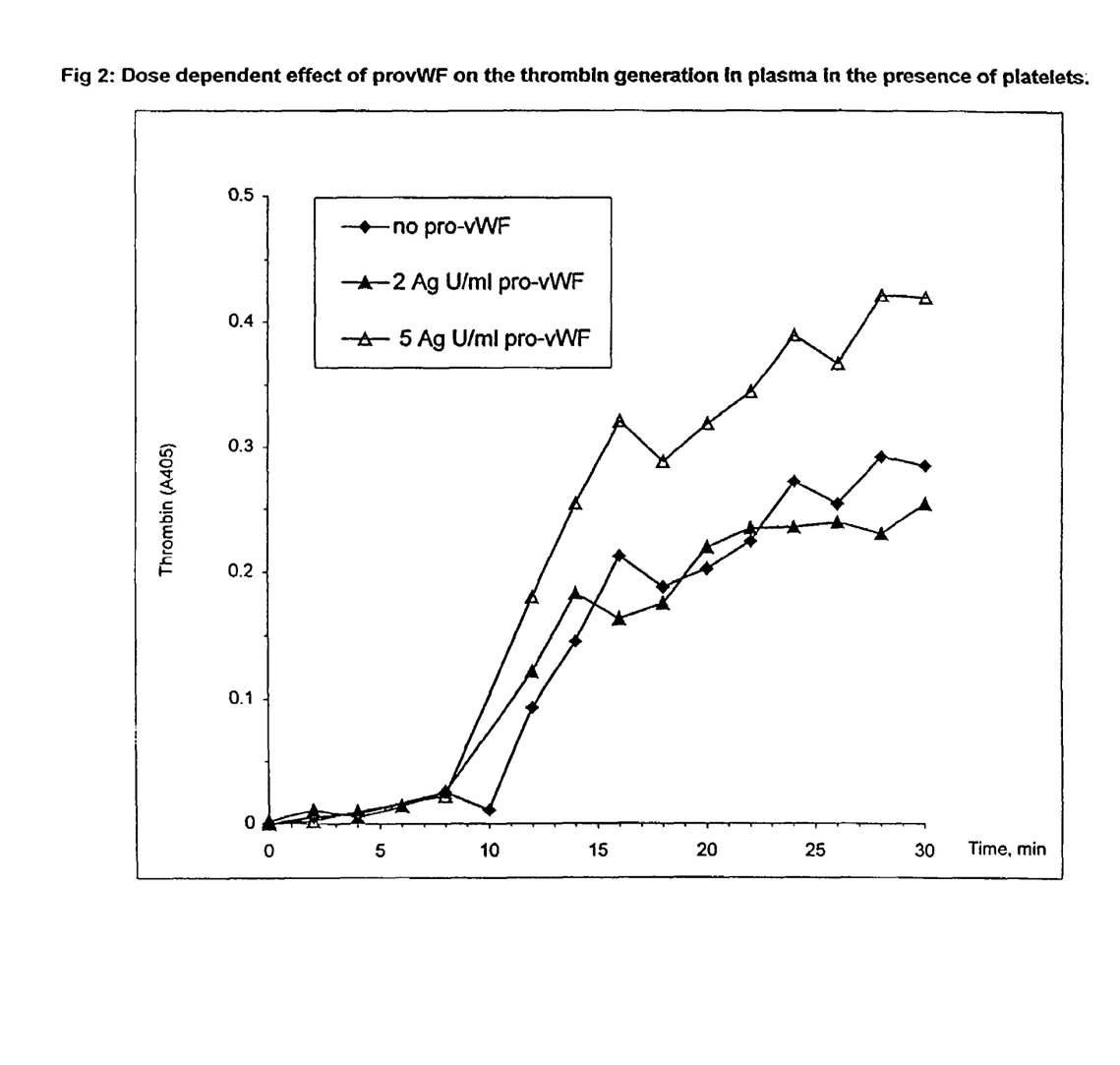
FIG. 2 shows the dose dependent effect of pro-vWF on the thrombin generation in plasma in the presence of platelets.

2. The Effect of provWF on the Thrombin Generation in Plasma in the Presence of Platelets The effect of a recombinant vWF preparation, which contained more then 90% provWF of the total vWF antigen on the thrombin generation was investigated in the system described by the Example 1. Washed platelets from an other severe vWD patient (Type III) and the isolated plasma sample of the same patient, reconstituted with 1 U/ml FVIIIC were used in the experiments. Recombinant provWF of 2 and 5 vWF-Ag U/ml (1 Ag U=the vWF antigen amount in 1 ml normal plasma) respectively, were added to the plasma samples and thrombin generation was compared with that of in the absence of vWF. FIG. 2 shows, that above a threshold of 2 vWF-Ag U/ml an increased thrombin generation was observed.

Example 3

Comparison of the in vivo Effect of a High provWF Containing Recombinant and a Plasma Derived vWF Preparation A vWF deficient dog (vWF antigen below the detection limit, and factor VIII activity about 50% of the normal) was anesthetized and infused with 35 Risto U/ml of the recombinant vWF used in the example 2, containing more then 90% of provWF. Prior to the infusion and 15, 30, 40 minutes, 1, 2, 3, 6, 24, 48, 72, an 95 hours post infusion plasma samples were taken. 95 hours later a plasma derived vWF preparation (Haemate HS—Behringwerke, Marburg, Germany) was added, and plasma samples were taken again at the same intervals after the infusion, as before. This plasma derived vWF preparation further contained Factor VIII:C, but no provWF and no ppvWF. The plasma samples were analyzed for total vWF antigen (Asserachrom ELISA, Boehringer), provWF and propeptide antigen (according to Borchiellini at al Blood 88, 2951, 1996), as well as for the thrombin generation potential, as described in Example 1. The thrombin potential is defined as the maximum thrombin concentration measured as described in Example 1.

Figure 3A:
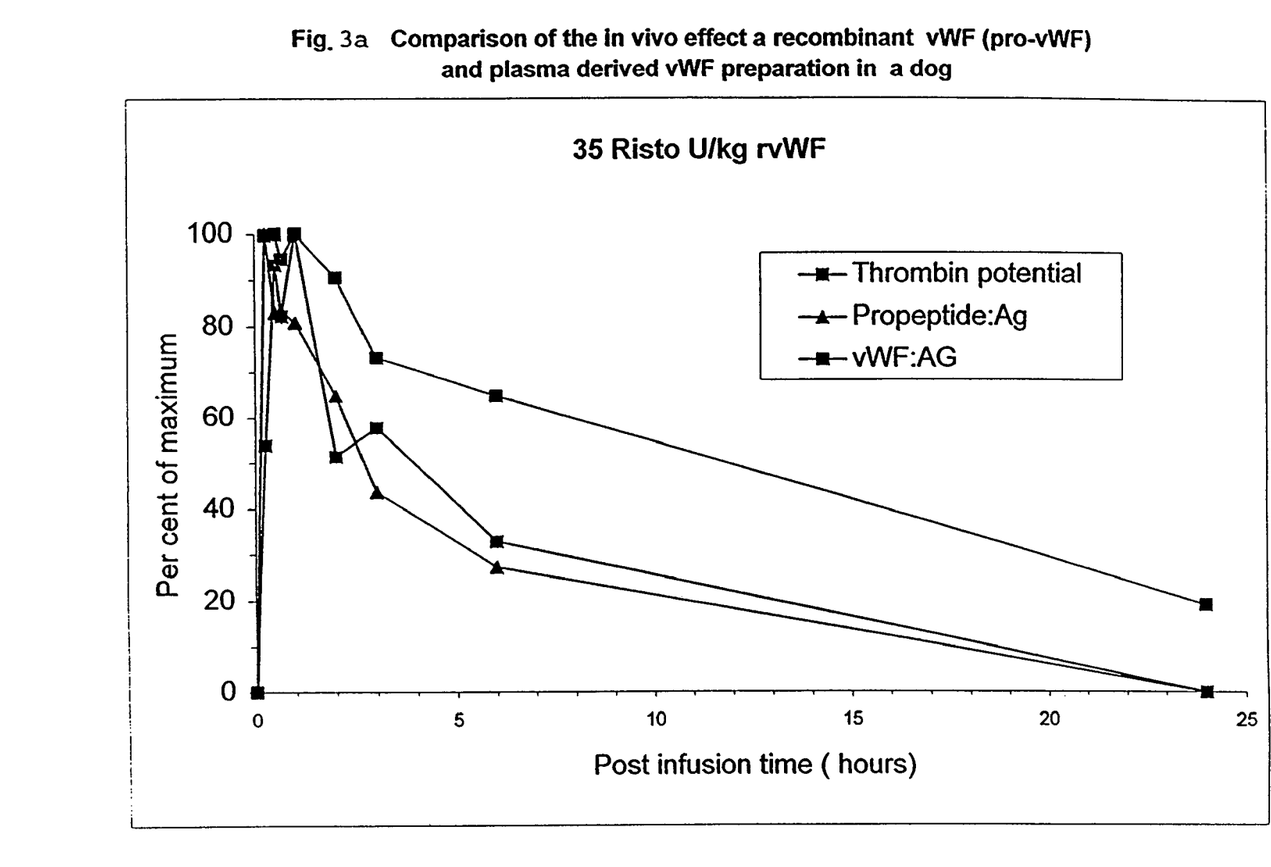
FIGS. 3a and 3b show the comparison of the in vivo effect of pro-vWF and plasma derived vWF in a dog.
Figure 3B:
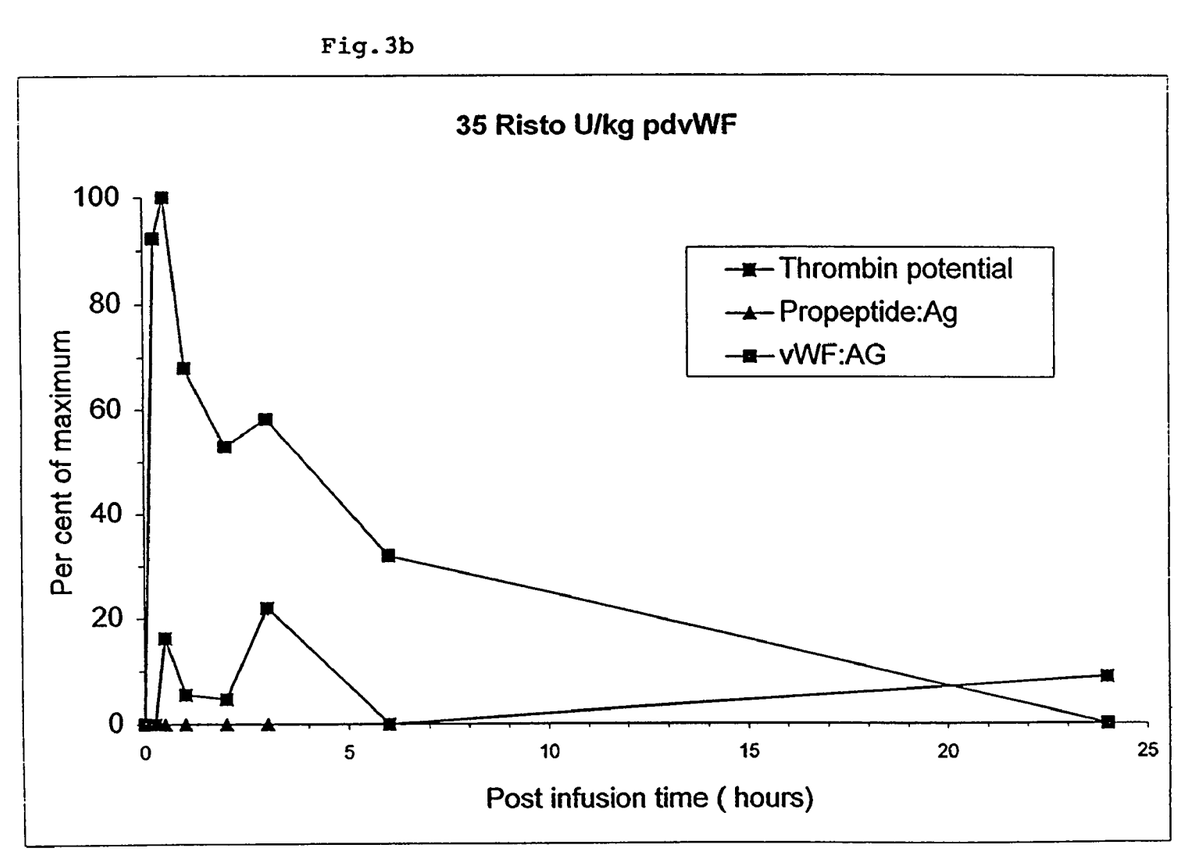

FIG. 3 shows the correlations of the various parameters, expressed as percent of maximum, regarding the initial values as zero.

Thrombin potential increased in parallel with the increase of propeptide after the treatment with a recombinant pro-vWF preparation. ELISA results showed, that a few percent of pro-vWF remained in the circulation after 15 minutes, and it could no longer be detected (data not shown), but a significant increase in the propeptide and vWF was observed. In contrast, no propeptide and also no substantial thrombin potential was observed in the dog after the plasma derived vWF infusion, despite the vWF antigen level increase.

The invention claimed is:

1. A method of treating a blood coagulation disorder comprising the step of administering a pharmaceutical preparation comprising an effective amount of a molecule selected from the group consisting of vWF-propeptide (pp-vWF) and pro-vWF to a patient.

2. The method according to claim 1, wherein the blood coagulation disorder is selected from the group consisting of von Willebrand's disease, phenotypic hemophilia, hemophilia A and factor VIII inhibitors.

3. The method according to claim 1, wherein the pharmaceutical preparation further comprises an effective amount of a hemostasis protein selected from the group consisting of mature vWF, factor VIII, activated blood coagulation factors, blood factors with factor eight inhibitor bypassing (FEIB) activity and FEIBA.

4. A method according to claim 3, wherein pro-vWF is complexed to factor VIII.

5. The method according to claim 3, wherein the thrombosis risk of the patient is reduced when compared to patients treated with a pharmaceutical preparation not comprising an effective amount of a molecule selected from the group consisting of pp-vWF and pro-vWF.

6. The method according to claim 1, wherein the pharmaceutical preparation further comprises an effective amount of a platelet component selected from the group consisting of collagen, platelet glycoprotein, a platelet, fibrinogen, fibrin, or heparin.

7. A method of treating a patient at risk of a blood coagulation disorder comprising the step of administering a pharmaceutical preparation comprising an effective amount of a molecule selected from the group consisting of vWF propeptide (pp-vWF) and pro-vWF to a patient, wherein the blood coagulation disorder is selected from the group consisting of von Willebrand's disease, phenotypic hemophilia, hemophilia A and factor VIII inhibitors.

* * * * *

UNITED STATES PATENT AND TRADEMARK OFFICE
CERTIFICATE OF CORRECTION

PATENT NO. : 7,557,188 B2  Page 1 of 1
APPLICATION NO. : 11/218406
DATED : July 7, 2009
INVENTOR(S) : Schwarz et al.

It is certified that error appears in the above-identified patent and that said Letters Patent is hereby corrected as shown below:

On the cover page, in column 1, change item (22), the filing date of the application, to read as follows:

(22)   Filed:      Sep. 1, 2005

Signed and Sealed this

Twenty-fifth Day of August, 2009

David J. Kappos
*Director of the United States Patent and Trademark Office*

UNITED STATES PATENT AND TRADEMARK OFFICE
CERTIFICATE OF CORRECTION

PATENT NO. : 7,557,188 B2
APPLICATION NO. : 11/218406
DATED : July 7, 2009
INVENTOR(S) : Schwarz et al.

It is certified that error appears in the above-identified patent and that said Letters Patent is hereby corrected as shown below:

On the cover page, should read as follows:

Item [*] Notice: Subject to any disclaimer, the term of this patent is extended or adjusted under 35 USC 154(b) by 145 days Delete the phrase "by 145 days" and insert -- by 97 days --

Signed and Sealed this

Third Day of November, 2009

David J. Kappos
*Director of the United States Patent and Trademark Office*